United States Patent
Fisher et al.

(10) Patent No.: US 6,953,817 B2
(45) Date of Patent: *Oct. 11, 2005

(54) DUAL COMPONENT DENTINAL DESENSITIZING DENTIFRICE

(75) Inventors: Steven W. Fisher, Middlesex, NJ (US); Marilou T. Joziak, South River, NJ (US); Richard J. Sullivan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/212,660

(22) Filed: Aug. 5, 2002

(65) Prior Publication Data

US 2004/0022746 A1 Feb. 5, 2004

(51) Int. Cl.[7] .................................................. A61K 7/16
(52) U.S. Cl. ........................... 524/52; 424/57; 433/215; 433/216
(58) Field of Search ..................... 424/52, 57; 433/215, 433/216

(56) References Cited

U.S. PATENT DOCUMENTS

| | | | |
|---|---|---|---|
| 3,105,798 A | * 10/1963 | Holliday et al. | 424/52 |
| 5,215,740 A | 6/1993 | Domke et al. | 424/52 |
| 5,702,686 A | 12/1997 | Maekawa et al. | 424/49 |
| 5,718,885 A | 2/1998 | Gingold et al. | 424/49 |
| 5,780,015 A | 7/1998 | Fisher et al. | 424/52 |
| 5,895,641 A | 4/1999 | Usen et al. | 424/52 |
| 5,939,052 A | 8/1999 | White et al. | 424/52 |
| 6,180,089 B1 | 1/2001 | Gambogi et al. | 424/52 |

FOREIGN PATENT DOCUMENTS

| | | |
|---|---|---|
| GB | 2188548 | 10/1987 |
| WO | WO9953893 | 10/1999 |
| WO | WO9955297 | 11/1999 |
| WO | WO0062749 | 10/2000 |
| WO | WO0145660 | 6/2001 |
| WO | WO0166074 | 9/2001 |

* cited by examiner

Primary Examiner—Frederick Krass
(74) Attorney, Agent, or Firm—Kristyne A. Bullock

(57) ABSTRACT

A two component dental composition is disclosed which eliminates or substantially reduces the discomfort and pain associated with dentinal hypersensitivity which composition comprises a first dentifrice component having a neutral pH in the range of about 6.5 to 7.5 buffered with a phosphate salt, a second dentifrice component having an alkaline pH in the range of 6.5 to 7.5 and at least one of the components containing a potassium ion releasable compound and a fluoride ion releasable salt, the first and second components being maintained separate from each other until dispensed and combined for application to teeth requiring relief from dentine hypersensitivity, whereby heightened desensitization is experienced by the user.

16 Claims, 2 Drawing Sheets

DUAL COMPONENT DENTINAL DESENSITIZING DENTIFRICE

BACKGROUND OF THE INVENTION

1. Field of the Invention

Figure 1:
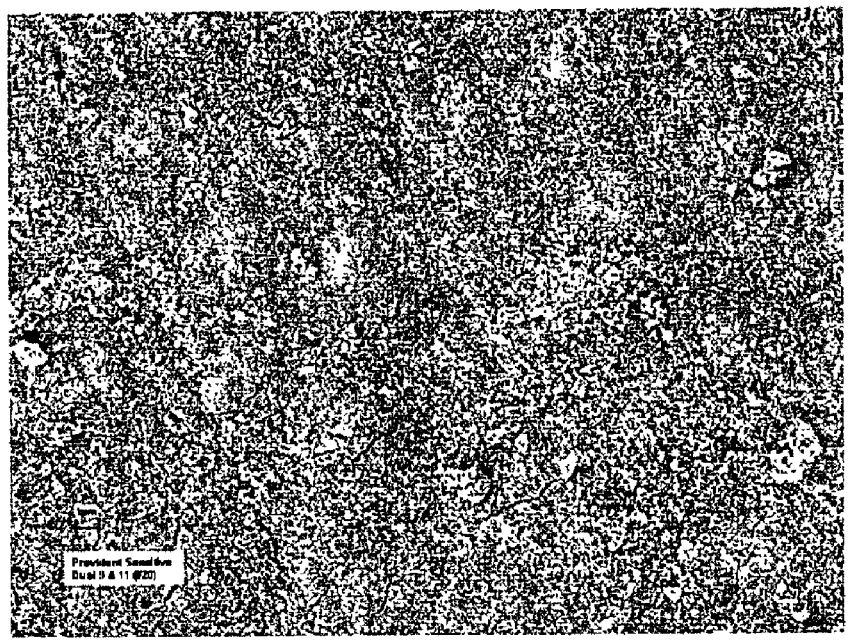

The present invention relates to a desensitizing dentifrice composition which eliminates or reduces the discomfort and pain associated with dentinal hypersensitivity and more particularly to a two-component desensitizing dental composition containing potassium salt desensitizing agents.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin.

Exposure of the dentine, which is generally due to recession of the gums, or loss of enamel, frequently leads to hypersensitivity. The art has determined that dentine tubules open to the surface have a high correlation with dentine hypersensitivity, Abs, J. Clin. Periodontal. 14,280–4 (1987). Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

It is known to the art that potassium salts are effective in the treatment of dentinal hypersensitivity. For example, U.S. Pat. No. 3,863,006 discloses that toothpastes containing potassium salts such as potassium nitrate desensitize the teeth after tooth brushing for several weeks. It is believed by those skilled in the art that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium ion into and out of the open dentine tubules, repeated application of the active ingredient is necessary to build up the necessary concentration in the vicinity of the pulpal nerves.

It is believed that the improved pain relief is obtained from the use of potassium salts in combination with gradual mineralization on the dentin surface which can either totally or partially occlude dentin tubules. Total occlusion will dramatically reduce fluid flow within the tubules which stimulates pain. Partial occlusion of the dentin tubules is believed to increase delivery of potassium ion inside the tooth because the inward diffusive flux is less dependent upon tubule radius than outward fluid flow (due to positive pulpal pressures) (See D H Pashley and W G Mathews, Archs. Oral Biol. (1993) 38, 577–582). Therefore, this enhanced delivery of potassium should enhance relief.

U.S. Pat. No. 6,180,089 discloses a dual component dentifrice comprised of separately housed dentifrice components of acidic and alkaline pH wherein at least one component contains a potassium salt. The components when combined before use exhibit unexpected improved effectiveness when applied to the teeth in obturating dentinal tubules with concomitant desensitization of teeth as compared to single component composition of neutral pH.

While the prior art discloses the use of various oral compositions for the treatment of dentinal hypersensitivity, there is still a need for additional compositions and methods which provide improved performance in the treatment of dentinal hypersensitivity along with increased consumer acceptance.

SUMMARY OF THE INVENTION

In accordance with the present invention there is provided a composition and method for the treatment of dentinal hypersensitivity using a multicomponent dentifrice comprised of two separately housed, semi-solid aqueous components; the first component buffered to maintain an alkaline pH of at least about 9.0 and preferably about 9.0 to about 12.0 and, the second component maintained at a pH of 6.5 to 7.5 with a phosphate salt buffer ingredient, at least one component containing a fluoride ion releasing salt and a potassium releasable salt compound in an orally acceptable vehicle in which the fluoride compound is present at a concentration sufficient whereby about 2500 to 8800 parts per million (ppm) fluoride is releasable from the compound so that upon mixing and combination of the components, a mixture having a pH of from about 6.5 to about 7.0 is formed, whereby upon repeated application of the mixture to the teeth increased relief from dentinal hypersensitivity is experienced by the user.

IN THE DRAWINGS

FIG. 1 is a SEM recorded at 2,000× magnification, of a dentin disk surface treated with a dual component dentifrice containing high concentrations of a fluoride salt which releases 5000 ppm fluoride ion (1.1% by weight) and potassium nitrate (5% by weight), wherein the first component is buffered to a pH of 6.5 and the second component adjusted to a pH of 9.5 with sodium hydroxide, the pH of the combined components being 7.5.

Figure 2:
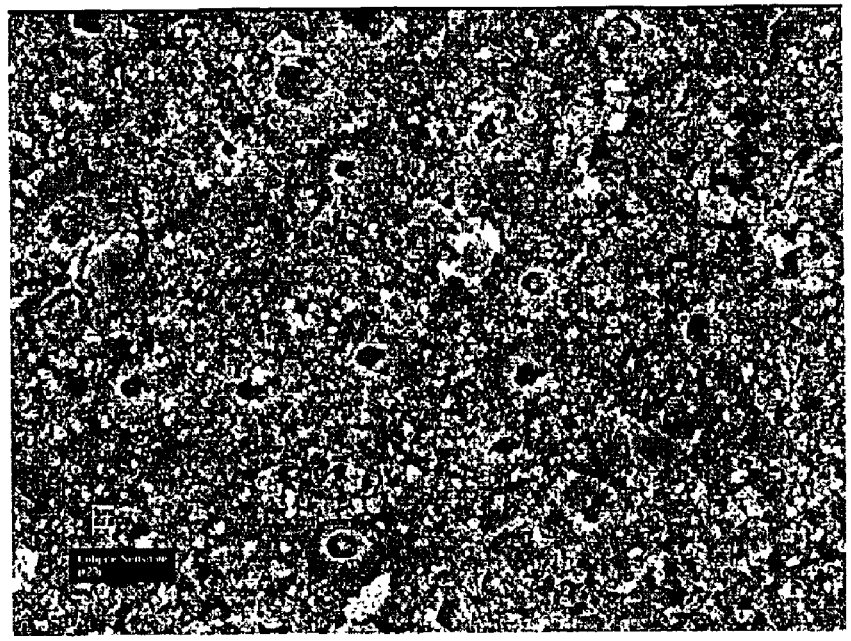

FIG. 2 is a SEM recorded at 2,000× magnification, of a dentin disk surface treated with the combined components of a comparative dual component dentifrice of the prior art (U.S. Pat. No. 6,180,089) containing 5% potassium nitrate and a fluoride containing salt which releases 1100 ppm fluoride ion wherein one component is maintained at alkaline pH and the second component maintained at an acid pH, the pH of the combined components being 7.0.

Figure 3:
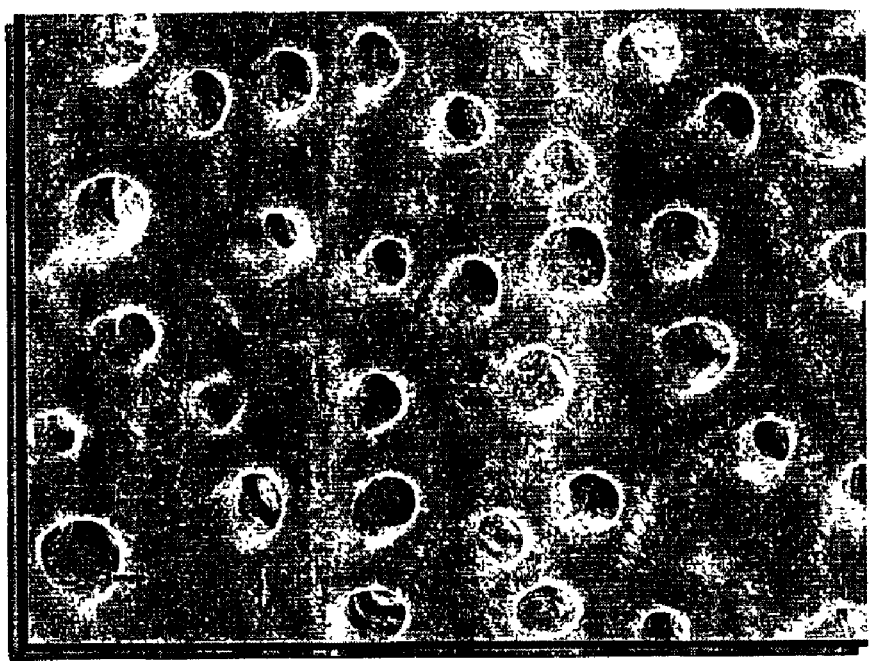

FIG. 3 is a scanning electron photomicrograph (SEM) recorded at 2,000× magnification of a dentin disk surface treated with a phosphate buffer solution.

DESCRIPTION OF THE PREFERRED EMBODIMENTS

In use, the components of the two component dentifrice of the present invention comprise a first dentifrice component maintained at an alkaline pH of about 9.0 to about 12 and preferably about 9.0 to 11.0, and a second dentifrice component buffered to maintain pH at a substantially neutral pH level of 6.5 to 7.0. The two components are preferably combined in approximately equal weight proportions, so that about one-half of the concentration of any particular ingredient within either component will be present when the components are combined and applied to the teeth, as by brushing. Both components are preferably formulated to have similar physical characteristics, so that the two components may be simultaneously delivered in the desired predetermined amounts by extrusion when separately housed in a multicompartmented tube or pump device.

To prepare the dentifrice component of the present invention having a substantially neutral pH, a buffering agent is incorporated in the dentifrice component which is normally prepared using as a vehicle which contains water, humectant, surfactant and an abrasive. The pH of such dentifrice is in the neutral pH range of about 6.5 to about 7.5 and preferably about 7.0 to about 7.5. The buffering agent is preferably a mixture of mono- and dibasic sodium phosphate salts and is incorporated in dentifrice component at a concentration of about 5 to about 10% by weight and preferably about 6 to about 10% by weight of in the component.

The dentifrice component having an alkaline pH is prepared having a composition similar to that of the buffered neutral pH component. The pH of the alkaline component is adjusted to a pH of about 9 to about 12 and preferably about 9.5.

An alkaline agent such as an alkali metal compound including sodium hydroxide, potassium hydroxide, sodium bicarbonate, sodium carbonate, N-sodium silicate (a 3.22 weight ratio of sodium silicate in 34.6% water available from PQ Corporation) is incorporated in the alkaline pH dentifrice component of the present invention in amounts in the range of about 0.5 to about 15% by weight, preferably about 1.0 to about 8% by weight and most preferably at about 1.0 to about 5.0% by weight of the component. Mixtures of the above alkali metal compounds may also be used. Sodium hydroxide is the preferred alkaline agent.

The humectant used in the preparation of the vehicle for the dentifrice components is generally a mixture of humectants, such as glycerol, sorbitol and a polyethylene glycol of molecular weight in the range of 200 to 1000, but other mixtures of humectants and single humectants may also be employed. The humectant content is in the range about of 10% to about 50% by weight and preferably about 20 to about 40% by weight of the dentifrice component. The water content is in the range of about 20 to about 50% by weight and preferably about 30 to about 40% by weight.

Thickeners used in the preparation of the dentifrice component vehicle include organic and inorganic thickeners. Inorganic thickeners which may be included in the dentifrice components include amorphous silicas such as Zeodent 165 available from Huber Corporation, and Sylox 15 from W. R. Grace.

Organic thickeners of natural and synthetic gums and colloids may also be used to prepare the dentifrice components of the present invention. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic thickener may be incorporated in the dentifrice components of the present invention at a concentration of about 0.5 to about 5% by weight and preferably about 1 to about 3% by weight. The organic thickener may be incorporated in the compositions of the present invention at a concentration of about 0.1 to about 3% by weight and preferably about 0.4 to about 1.5% by weight.

Surfactants may be incorporated in the dentifrice components to provide foaming properties. The surfactant is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

The surfactant agent is generally present in the dentifrice component compositions of the present invention at a concentration of about 0.5 to about 10.0% by weight and preferably about 1.0 to about 5.0% by weight.

Abrasives may be incorporated in the dentifrice components of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, calcined alumina and bentonite.

The concentration of abrasive in the dentifrice component compositions of the present invention will normally be in the range of 5 to about 40% by weight and preferably about 10 to 25% by weight.

The source of desensitizing potassium ion is generally a water soluble potassium salt including potassium nitrate, potassium citrate, potassium chloride, potassium bicarbonate and potassium oxalate with potassium nitrate being preferred. The potassium salt is generally incorporated in one or more of the dentifrice components at a concentration of about 1 to about 20% by weight and preferably about 3 to about 10% by weight.

Fluoride ion releasing salts are incorporated in the dentifrice of the present invention and are characterized by their ability to release fluoride ions in water. It is preferable to employ a water soluble fluoride salt providing about 1000 to about 9000 ppm of fluoride ion, and preferably about 2500 to about 8800 ppm of fluoride ion. Suitable examples of fluoride ion releasing salts include water soluble inorganic metal salts, for example, sodium fluoride, potassium fluoride, sodium monofluorophosphate, stannous fluoride and sodium fluorosilicate. Sodium fluoride, sodium monofluorophosphate and stannous fluoride are preferred fluoride ion releasing salts.

Pyrophosphate salts having anticalculus efficacy useful in the practice of the present invention include water soluble salts such as dialkali or tetraalkali metal pyrophosphate salts such as $Na_4P_2O_7$ (TSPP), $K_4P_2O_7$, $Na_2K_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate.

The pyrophosphate salts are incorporated in the dentifrice composition of the present invention at a concentration of about 0.5 to about 2.0% by weight, and preferably about 1.5 to about 2% by weight and the polyphosphate salts are incorporated in the dentifrice composition of the present invention at a concentration of about 1.0 to about 7.0% by weight.

Colorants such as pigments and dyes may be used in the practice of the present invention. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium slat of 4-{[4-(N-ethyl-p-sulffobenzyno)-phenyl]-(4-hydroxy-2-sulfoniumphenyl)-mewthylene}-[1-(N-ethyl-N-p-sulfobenzyl)-(x)-3,5-cyclohexadienimine], FD&C Blue No. 1 (disodium salt of dibenzyldiethyldiaminotriphenylcarbinol trisulfonic acid of indigotin) and mixtures thereof in various proportions. The concentration of the dye for the most effective result in the present invention is present in the dentifrice composition in an amount from about 0.0005 percent to about 2 percent of the total weight.

A striped dentifrice product may be obtained using the dual component dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both the pigments and dyes discussed above.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.01% to 5% or more of the preparations.

Antibacterial agents are non-cationic antibacterial agents based on phenolic and bisphenolic compounds, halogenated diphenyl ethers such as Triclosan, benzoate esters and carbanilides as well as cationic antibacterial agents such as chlorhexidine digluconate. Such antibacterial agents can be present in quantities of from about 0.03 to about 1% by weight of the particular component.

When noncationic antibacterial agents or antibacterial agents are included in any of the dentifrice components, there is also preferably included from about 0.05 to about 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to about 3% by weight.

To prepare either of the dentifrice components of the present invention, generally the humectants, for example, propylene glycol, polyethylene glycol ingredients, are dispersed with any organic thickeners, sweetener, pigments such as titanium dioxide and any polyphosphates included as anti-calculus ingredients. Water is then added into this dispersion along with any antibacterial agent such as Triclosan, any antibacterial enhancing agent such as Gantrez and any anticalculus additional agents. In the first neutral pH component a fluoride ion source desensitizing agent and phosphate buffering agent is added. In the second component an ingredient to adjust the pH to an alkaline level is added, such as sodium hydroxide. These ingredients are mixed until a homogenous phase is obtained for each component. Thereafter inorganic thickener, silica abrasive, flavor and surfactant ingredients are added and the ingredients mixed at high speed under vacuum of from about 20 to 100 mm of Hg. The resultant product, in the case of each component, is a homogeneous, semi-solid, extrudable paste product.

The multicomponent dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a pump or a tube, having collapsible sidewalls, as disclosed in U.S. Pat. Nos. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following example is further illustrative of the present invention, but it is understood that the invention is not limited thereto. All amounts and proportions referred to herein and in the appended claims are by weight, unless otherwise stated.

EXAMPLE

A two component (Component A and B) desensitizing dentifrice of the present invention was prepared, designated "Dentifrice X", Component A having neutral pH (6.5) and a Component B having an alkalin pH (9.5). When combined in equal amounts for tooth brushing, Dentifrice X had a pH of 7.5 in a 1:3 slurry with water. The ingredients of Components A and B are listed in Table I below.

TABLE I

| | Dentifrice X | |
|---|---|---|
| | Weight % | |
| Component Ingredients | A | B |
| Deionized Water | 32.995 | 36.895 |
| Sodium Fluoride | 1.105* | 1.105* |
| Potassium Nitrate | 5.00 | 5.00 |
| Glycerin | 18.000 | 18.000 |
| Polyethylene glycol 600 | 3.000 | 3.000 |
| Xanthan gum | 7.000 | 7.000 |
| Carboxymethyl cellulose | 0.500 | 0.500 |
| Sorbitol 70% NC | 5.00 | 5.000 |
| Sodium saccharin | 0.400 | 0.400 |
| Titanium Dioxide | — | 1.000 |
| Pluronic F-127 | 2.000 | 2.000 |
| Sodium Hydroxide (50%) | — | 1.000 |
| Sodium Phosphate Mono | 4.000 | — |

TABLE I-continued

Dentifrice X

| Component Ingredients | Weight % A | Weight % B |
|---|---|---|
| Sodium Phosphate Dibasic | 3.500 | — |
| FD & C Blue #1 (1.25% solution) | — | 0.300 |
| Zeodent 115 | 20.000 | 15.000 |
| Zeodent 165 | 1.000 | 1.500 |
| Sodium bicarbonate | — | 2.500 |
| N-silicate | — | 3.800 |
| Sodium lauryl sulfate | 1.500 | 1.500 |
| Flavor | 1.100 | 1.100 |

*Releases 5000 ppm fluoride ion

In the preparation of Dentifrice I, the glycerin, polyethylene glycol and organic thickeners were dispersed in a conventional mixer until the mixture became a slurry, which was smooth in appearance. Color and sweetener were dispersed in this slurry before the addition of water. In the preparation of Component A, potassium nitrate was then dispersed in this slurry. In the preparation of Component B, sodium hydroxide was then dispensed in the gel phase. This mixture was mixed for 20 to 30 minutes producing a homogeneous gel phase. The mixture was added to a vacuum mixer and cooled below 105° F. Zeodent 115, Zeodent 165 and sodium bicarbonate were then added and mixed for 10 to 30 minutes at high speed under a vacuum of about 50 mm Hg, providing a homogenous mixture. The sodium lauryl sulfate and flavor were then added to the individual dentifrice components which was followed by mixing another 5–15 minutes under vacuum of 50 mm Hg to prepare the resultant component product.

The desensitizing efficacy of the two component Dentifrice X was evaluated using 4.25 mm×4.25 mm square dentin disks of 750 $\mu$m thickness cut from extracted human molars. The disks were prepared for treatment by etching with 6% citric acid for 2 minutes to remove any surface smear.

For purposes of comparison the procedure of the Example was repeated with another group of similarly prepared disks using a dual component dentifrice designated "Dentifrice Y", comparable to that of U.S. Pat. No. 6,180,089 in which the alkaline component designated "Component C" had a pH of 9.5 and the acidic component designated "Component D" had a pH of 5.2. The ingredients of Components C and D of Dentifrice Y are listed in Table II below.

As a control, the procedure of the Example was repeated using a phosphate buffer solution as the treatment which treatment was designated "Control". The ingredients of the phosphate buffer solution are listed in Table III below.

The ingredients of Components C and D of Dentifrice Y are listed in Table II below.

TABLE II

Dentifrice Y

| Component C | | Component D | |
|---|---|---|---|
| Ingredient | % | Ingredient | % |
| Deionized water | 29.57 | Dionized water | 25.66 |
| Potassium nitrate | 10.000 | Anhydrous citric acid | 0.531 |

TABLE II-continued

Dentifrice Y

| Component C | | Component D | |
|---|---|---|---|
| Ingredient | % | Ingredient | % |
| Glycerin | 25.48 | Sodium citrate | 2.657 |
| PEG 600 | 3.00 | Stannous chloride | 0.600 |
| Xanthan NF | 0.700 | Stannous fluoride | 0.908* |
| Sodium carboxymethyl cellulose | 0.50 | Glycerin | 33.704 |
| Sodium saccharin | 0.4 | Xanthan | 0.500 |
| Titanium dioxide | 2.00 | Sodium carboxymethyl cellulose 2000S | 0.700 |
| Pluoronic F-127 | 1.00 | Sodium saccharin | 0.400 |
| Zeodent 115 | 15.00 | Tetrasodium pyrophosphate | 0.500 |
| Zeodent 165 | 1.75 | FD & C Blue #1 (1.25% soln.) | 0.240 |
| Sodium bicarbonate | 5.00 | PEG 40 oil | 6.00 |
| Sodium hydroxide | 3.00 | Pluoronic F-127 | 2.00 |
| Flavor stannous plus | 1.10 | Zeodent 115 | 20.00 |
| Sodium lauryl sulfate | 1.5 | Zeodent 165 | 3.00 |
| | | Flavor | 1.100 |
| | | Sodium lauryl sulfate | 1.500 |
| Totals | 100 | | 100 |

*Releases 2200 ppm fluoride ion. Fluoride ion delivery of Dentifrice Y is 1100 ppm when Component C and D are combined for use.

TABLE III

Phosphate Buffer Solution

| Ingredient | Wt. % | Millimoles |
|---|---|---|
| Sodium phosphate mono | 0.0087 | 0.63 |
| CaCl$_2$ | 1.1456 | 1.06 |
| NaCl | 0.877 | 150.0 |

The etched disks were then treated by separately brushing the discs for a 60 second period with either Dentifrice X or Y or the phosphate buffer solution (control).

The surface composition of the treated disks were then subjected to Electron Spectroscopy for Chemical Analysis (ESCA) and Scanning Electron Microscopy (SEM) analysis. The ESCA results are recorded in Table IV below as an average for each group. The percentage of nitrogen on the dentin surface is generally attributed to the amount of exposed collagen material which is an integral part of the dentin structure. The reduced amount of nitrogen is indicative of a surface coating, and the higher the amount of calcium ion, the greater the degree of tubular occultation.

TABLE IV

| Dentifrice | ESCA Analysis Atomic Percent | | | | | | | | | P/Ca Ration |
|---|---|---|---|---|---|---|---|---|---|---|
| | C | O | N | Ca | P | Si | Na | Sn | F | |
| X | 33.20 | 42.63 | 3.78 | 7.66 | 6.32 | 4.88 | 0.80 | 0.19 | 0.55 | 0.82 |
| Y | 27.76 | 47.27 | 2.45 | 4.73 | 4.10 | 11.39 | 1.02 | 1.16 | 0.11 | 0.86 |
| Control | 59.69 | 22.78 | 14.72 | 1.17 | 0.99 | 0.68 | — | — | — | 0.85 |

The results recorded in Table IV indicate that the amount of deposit formed on the surface of the dentin disks treated with the combined components of Dentifrice X of the present invention is substantially greater than the disks treated with comparative Dentifrice Y, indicating a significantly greater degree of tubular obturation would be experienced with the use of Dentifrice X as compared to Dentifrice Y.

The SEM photomicrographs taken of the dentin surfaces subjected to the brushing treatments are shown in FIGS. 1–3 respectively. Examination of the SEM of the Dentifrice X treated dentin disk surface, (FIG. 1), indicates that dentinal tubule obturation was substantially complete as compared to treatment with comparative dual component Dentifrice Y as indicated by examination of the photomicrograph of FIG. 2. The Control treatment of the dentin disks using an phosphate buffer solution as shown in the SEM of FIG. 3 indicates a limited amount of dentinal tubule obturation.

The ESCA and the SEM results all provide evidence that the unique combination of the neutral and alkaline potassium ion containing dentifrice components in combination with high releasable fluoride ion concentration levels effects an unexpected significant improvement in the remediation of dentinal hypersensitivity.

What is claimed is:

1. A two component dental composition which reduces the discomfort and pain associated with dentinal hypersensitivity which composition comprises a first dentifrice component having a neutral pH in the range of about 6.5 to 7.5, the pH being buffered with a phosphate salt, a second dentifrice component having an alkaline pH in the range of about 9 to about 12, and at least one of the components containing a fluoride ion releasing salt and a densensitizing potassium ion releasing salt, the first and second components being maintained separate from each other until dispensed and combined for application to teeth requiring relief from dentine hypersensitivity, whereby desensitization is experienced by the user.

2. The composition of claim 1 wherein each component contains a fluoride ion releasing salt and a potassium ion releasing salt.

3. The composition of claim 1 wherein the potassium ion releasing salt is potassium nitrate.

4. The composition of claim 1 wherein the fluoride ion releasing salt present in the two component composition delivers a fluoride ion concentration of about 2500 to about 8800 ppm.

5. The composition of claim 1 wherein the fluoride ion releasing salt is sodium fluoride.

6. The composition of claim 1 wherein the alkaline dentifrice component is an aqueous dentifrice having a pH of about 9 to about 11.

7. The composition of claim 1 wherein the pH of the neutral pH dentifrice component is buffered with a sodium phosphate salt.

8. The composition of claim 1 wherein the pH of the alkaline dentifrice component is adjusted with sodium hydroxide.

9. A method for reducing the discomfort and pain associated with dentinal hypersensitivity which comprises preparing (1) a first dentifrice component having a neutral pH buffered with a phosphate salt in the range of about 6.5 to about 7.5 and (2) a second dentifrice component having an alkaline pH in the range of about 9 to about 12, at least one of the components containing a desensitizing potassium ion releasing salt and a fluoride ion releasing salt, separately housing the first and second components, dispensing the first and second components and combining the dispensed components for application to teeth requiring relief from dentine hypersensitivity and thereafter applying the combined components to the teeth whereby desensitization is experienced by the user.

10. The method of claim 9 wherein each component contains a fluoride ion releasing salt and a potassium ion releasing salt.

11. The method of claim 9 wherein the potassium ion releasing salt is potassium nitrate.

12. The method of claim 9 wherein the fluoride ion releasing salt present in the combined components delivers a fluoride ion concentration of about 2500 to about 8800 ppm.

13. The method of claim 9 wherein the fluoride ion releasing salt is sodium fluoride.

14. The method of claim 9 wherein the alkaline dentifrice component is an aqueous dentifrice having a pH of about 9 to about 11.

15. The method of claim 9 wherein the pH of the alkaline dentifrice component is adjusted with sodium hydroxide.

16. The method of claim 9 wherein the pH of the neutral pH dentifrice is buffered with a sodium phosphate salt.

* * * * *